United States Patent [19]

Gordon

[11] Patent Number: 5,691,194

[45] Date of Patent: *Nov. 25, 1997

[54] METHOD AND APPARATUS FOR IN VITRO FERTILIZATION

[75] Inventor: Jon W. Gordon, New York, N.Y.

[73] Assignee: Mount Sinai School of Medicine of the City University of New York, New York, N.Y.

[*] Notice: The term of this patent shall not extend beyond the expiration date of Pat. No. 5,512,476.

[21] Appl. No.: 718,902

[22] Filed: Sep. 24, 1996

Related U.S. Application Data

[60] Division of Ser. No. 414,739, Mar. 31, 1995, Pat. No. 5,627,066, which is a continuation-in-part of Ser. No. 125,084, Sep. 22, 1993, Pat. No. 5,512,476, which is a continuation of Ser. No. 699,745, May 14, 1991.

[51] Int. Cl.$^6$ ............................................. C12M 3/00
[52] U.S. Cl. ........................ 435/287.1; 435/288.3; 435/288.4; 435/289.1; 435/305.1; 435/305.2; 422/102; 600/33; 600/35
[58] Field of Search ................. 435/287.1, 288.3, 435/288.4, 289.1, 305.1, 305.2; 422/102; 600/33, 35

[56] References Cited

U.S. PATENT DOCUMENTS

| 5,484,731 | 1/1996 | Stevens | 435/305.3 |
| 5,512,476 | 4/1996 | Gordon | 435/240.26 |
| 5,627,066 | 5/1997 | Gprdon | 435/2 |

*Primary Examiner*—David A. Redding
*Attorney, Agent, or Firm*—Brumbaugh, Graves, Donohue & Raymond

[57] ABSTRACT

This invention relates to a method and apparatus for concentrating motile sperm from a sperm sample, including concentrating sperm in the vicinity of one or more oocytes for in vitro fertilization. The method comprises placing a volume of fertilization medium in a container, said container having at least one microchamber and being shaped such that the fertilization medium, when placed in the container, fills the microchamber and a portion of the container outside of the microchamber, such that when a sperm sample is placed in the medium outside the chamber motile sperm swim into the microchamber, where they may be harvested or, if an oocyte is in the microchamber, in vitro fertilization occurs.

25 Claims, 3 Drawing Sheets

METHOD AND APPARATUS FOR IN VITRO FERTILIZATION

"This is a divisional of application Ser. No. 08/414,739 filed on Mar. 31, 1995 now U.S. Pat. No. 5,627,066, which is a continuation-in-part of U.S. patent application Ser. No. 08/125,084, filed Sep. 22, 1993 now U.S. Pat. No. 5,512, 476, which is a continuation of U.S. patent application Ser. No. 07/699,745, filed May 14, 1991.

BACKGROUND OF THE INVENTION

This invention relates to a method and apparatus for concentrating motile sperm from a sperm sample, including concentrating sperm in the vicinity of one or more oocytes for in vitro fertilization.

Infertility in man and animals can result from many causes and is frequently associated with low sperm counts, low sperm motility and low percentages of viable, motile sperm. One approach to overcoming these problems is in vitro fertilization ("IVF"), i.e., the combination of sperm and oocyte in a controlled and observable environment outside the body.

As presently practiced, in vitro fertilization generally involves the preliminary separation of healthy, motile sperm from less healthy or non-motile sperm by methods such as Percoll gradients or "swim-ups (Laufer et al., in Infertility, Serbel, M. M. eds., Appleton & Lange 1990)." Such fractionation steps are carried out in all cases, including those where sperm are normal (e.g., infertility due to pathology in the female's reproductive system). This measure is taken because even normal semen samples contain substantial numbers of immotile or dead sperm and epithelial cells, and these extraneous cells can interfere with interaction of the motile sperm with the eggs. In addition to removal of unwanted sperm, however these sperm fractionation techniques result in substantial losses of motile sperm as well, and thus introduce their own problems which may lead to the failure of in vitro fertilization. Indeed, in situations where sperm counts are very low (e.g. less than $10^6$ motile sperm per milliliter of ejaculate), fractionation may yield no detectable motile sperm.

Still another problem with standard sperm preparation techniques is that they all require centrifugation of the sample. Centrifugation can damage sperm (Aitken, R. J., and Clarkson, J. S., 1988. J. Androl. 9:367–376), and in some cases can lead to destruction of all competent sperm in a sample.

Once the sperm fraction to be used is obtained, the sperm are added to a sample dish containing a small number of oocytes (generally from 1 to 2) in liquid medium. Animal studies have shown that insemination in very small volumes of the liquid medium or "microdrops" can improve the efficiency of egg:sperm interaction and reduce the sperm:egg ratio needed for fertilization (Bavister, J. Exp. Zool. 210:259–264 1979). However, in human IVF, microdrops are not used because such drops are subject to rapid fluctuations of pH and/or changes in osmolarity due to evaporation. Moreover, the smaller the volume of a microdrop, the greater the requirement that competent sperm be separated from extraneous cells and debris. Thus, standard IVF procedures usually entail insemination of eggs in 2 milliliters of medium. Laufer et al.

These relatively large volumes necessitate insemination with large numbers of sperm ($1–2\times10^5$ or more) in order to assure fertilization. However, when the sperm sample is abnormal or when many eggs are obtained, the loss during fractionation can result in insufficient numbers of motile sperm for subsequent insemination. This problem is particularly severe when the sperm count is low and/or the percentage of motile sperm in the sample is low.

In vitro fertilization also includes methods whereby a sperm cell is directly injected into the egg. As with other IVF methods, fractionation (usually by Percoll Gradients) is necessary in order to obtain individual motile sperm suitable for injection into the egg. Once again, where sperm counts are very low, fractionation may yield no sperm suitable for direct injection.

There thus exists a need in the art for a means for concentrating motile sperm from a sperm sample, for example for use in an in vitro fertilization technique which provides high fertilization efficiency without a preliminary sperm fractionation step being necessary. It is the object of the present invention to provide a method and apparatus to meet this need.

SUMMARY OF THE INVENTION

In accordance with the invention, a method and apparatus are provided for in vitro fertilization without conventional fractionation. The method and apparatus are suitable both for in vitro fertilization of an egg, and for the collection of one or more motile sperm for subsequent insemination, for example by directly injecting the sperm into the egg.

According to the invention, a specially shaped culture dish is used which contains at least one small chamber (hereinafter referred to as a "microchamber" or an "oocyte chamber"). The microchamber is shaped, sized and positioned such that it forms only a portion of the culture dish, and such that when the dish is in use liquid fills not only the oocyte chamber but extends outside of the chamber into at least a portion of the remainder of the dish.

A sperm example, particularly an unfractionated sperm sample, is placed in the culture liquid in the dish at a position remote from the microchamber(s), for example in the center of the dish in the situation where the oocyte chamber(s) is located at the periphery of the dish. Motile sperm tend to move rapidly toward and into the chamber(s), thus resulting in an in situ separation of motile from non-motile sperm. Because of the shape of the microchambers, once the sperm have entered the microchamber(s), they tend to remain concentrated in the microchambers. If an oocyte has been placed in the microchamber(s), high efficiency in vitro fertilization is thereby achieved. Alternatively, the method and apparatus according to the invention can be advantageously employed even where no oocytes are placed in the microchamber(s), in which case the invention permits the separation and collection of motile sperm for later insemination outside of the microchamber, e.g., as by direct injection of sperm into the egg.

A culture dish according to the invention has one or more microchambers formed on the interior surface of the base portion of the dish. Each microchamber has a volume which exceeds the volume of an oocyte to be fertilized but is small enough to provide for facile fertilization. In general, the oocyte chamber will have a volume which exceeds the volume of the oocyte by from 800% to 2,000%. The microchambers may be disposed about the periphery of a central circular region of the dish having a diameter of from 0.5 to 3 cm., or on a central plateau region.

DETAILED DESCRIPTION OF THE INVENTION

The present invention provides for both separation of sperm and isolation of oocytes within a low volume of fertilization medium in a single-step procedure.

EXAMPLE 1

Figure 1:
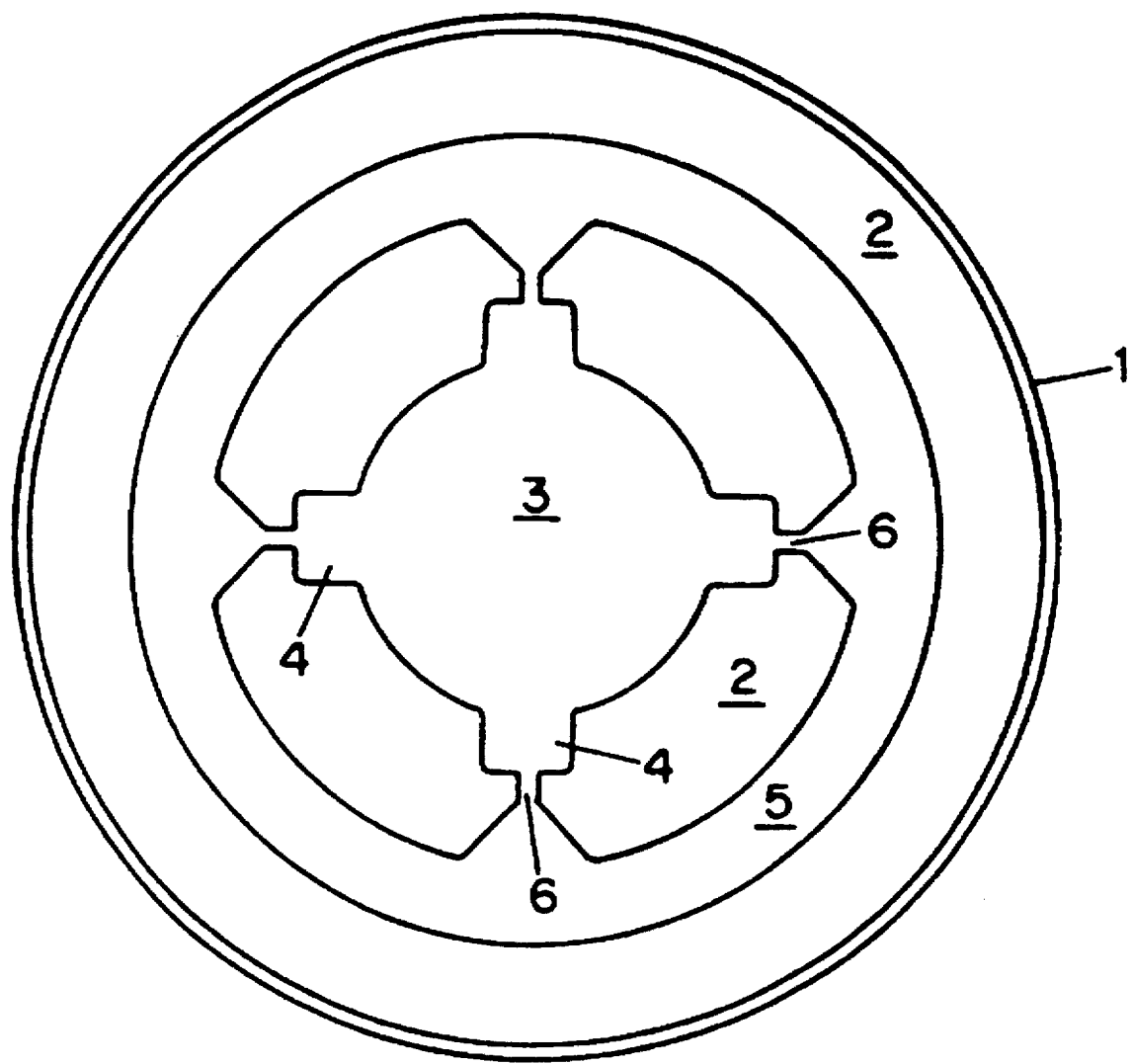
FIG. 1 shows an embodiment of the invention in which the oocyte chambers are formed by shaping the periphery of the microdrop.

The efficiency of this procedure has been demonstrated using a prototype fertilization microchamber as shown in FIG. 1.

In FIG. 1, a conventional culture dish is shown from above. The dish consists of side portion 1 which extends about the entire edge of the dish and a base portion 2. A microdrop of culture medium 3 was placed at the center of the interior surface of the base portion 2 and oocytes chambers 4 were formed by exploiting the adhesive properties of the dish surface to form the microdrop in this shape using a plastic micropipet tip. A ring of culture medium 5 was placed around the microdrop, and channels of medium 6 were formed to connect each oocyte chamber 4 to the ring of culture medium 5. The dimensions of the various portions of the experimental device are shown in Table 1.

TABLE 1

Dimensions of Experimental Paradigm of FIG. 1

| | |
|---|---|
| Diameter of culture dish base portion | 80 mm |
| Diameter of central microdrop | 40 mm |
| Volume of central microdrop | 100 µl |
| Dimensions of oocyte chambers | 150 µm W × 200 µm L |
| Width of outer ring of medium | 10 mm |
| Volume of outer ring of medium | 200 µl |

To test the efficacy of this design, mouse oocytes (having a diameter of about 80 µM) were placed in each of the four oocyte chambers formed in a microdrop of the medium, a sample of unfractionated frozen-thawed mouse sperm was added to the center of the microdrop and an oil drop was placed over the top to maintain the medium in place. Material tended to flow through the channels 6 from the central microdrop 3 to the outer ring 5, and this flow kept the oocytes in place within the oocyte chambers. The results of using this design for in vitro fertilization were a five-fold increase in fertilization efficiency.

EXAMPLE 2

The individual construction of a "custom" in vitro fertilization dish for each use is not really practical, both because some skill is involved in creating the oocyte chambers and channels and because the process is time consuming. Further, it was found that imperfectly balanced surface tension between the central microdrop and the outside ring can damage the oocytes. A culture dish suitable for mass production was therefore designed in which the principles embodied in the mouse experiment described above could be more routinely practiced.

Figure 2:
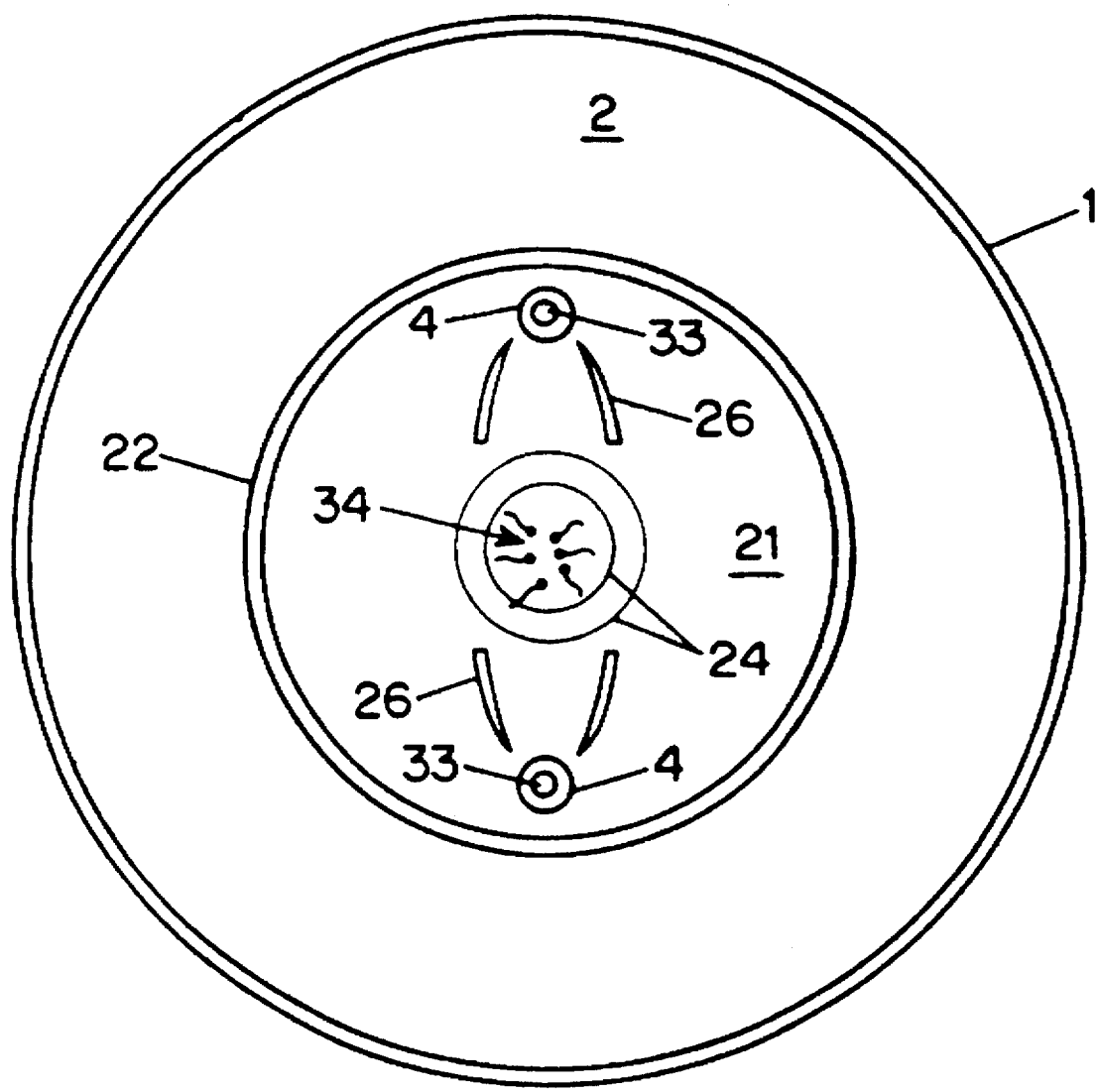
FIG. 2 shows a top view of a culture dish in accordance with the invention.

FIG. 2 shows a top view of a culture dish particularly adapted for use in the invention. In this culture dish there are two oocyte chambers 4 disposed at opposite sides of a circular region 21 and inside a wall member 22 which defines the edge of the microdrop of medium.

It will be understood, however, that the number of oocyte chambers may be greater, with 2 to 60 being the normal range of oocytes available for in vitro fertilization attempt.

The central circular region 21 advantageously has a central depression 31 (FIG. 3) so that a ridge 32 is formed between the center of the central circular region 21 and the oocyte chambers 4. The diameter of the central circular region 21 is advantageously from 0.5 to 30 mm, preferably 10 to 20 mm.

In use, a microdrop of medium is placed within the wall member 22. The volume of the microdrop will depend on the diameter of the central circular region 21, the depth of the central depression 31, if present, and the volume and number of the oocyte chambers 4, but will generally be on the order of 80 to 120 µl. As discussed below, higher volumes can be used if guide members are present to direct the sperm. Oocytes 33 are placed in the oocyte chambers 4 and a sperm sample 34 is placed in the center of the central circular region 21. The central circular region 21 may have rings 24 (FIG. 2) printed on it to help define the volume of sperm to be added. The number of sperm added is generally from 8,000 to 12,000 in volumes of 8–12 µl.

After addition of the sperm, the central circular region 21 may be covered using a top 35 which overlaps the wall member 22. The dish is then allowed to stand for a period of time (usually 10 to 20 hours) to allow healthy, motile sperm to swim to the oocyte chambers at the edge of the central circular region and fertilize the oocytes present therein.

Figure 4:
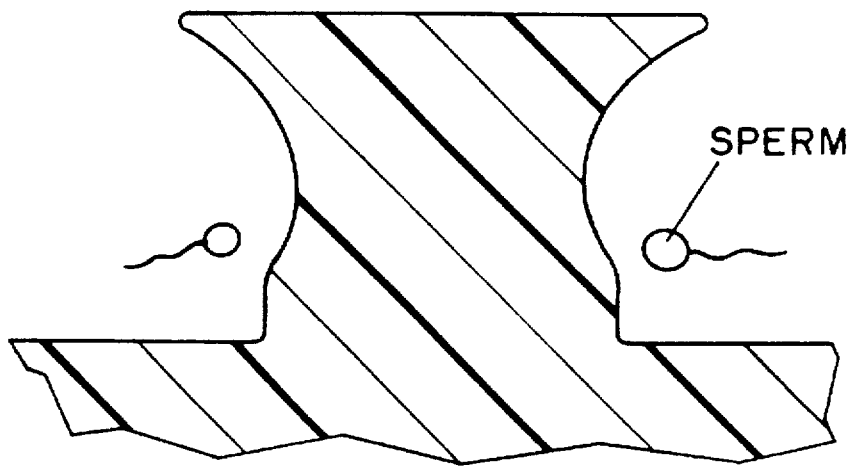
FIG. 4 shows a sectional view through a T-shaped guide member.

The culture dish according to the invention may also include guide members 26 disposed on the surface of the central circular region 21. These guide members tend to direct motile sperm toward those portions of the periphery where oocyte chambers exist and thus enhance the speed and frequency of fertilization. Preferred guide members have T-shaped cross sections (FIG. 4). The use of guide members facilitates the use of larger volumes in the "microdrop" with volumes as high as 1–2 ml being potentially useful.

Figure 3:
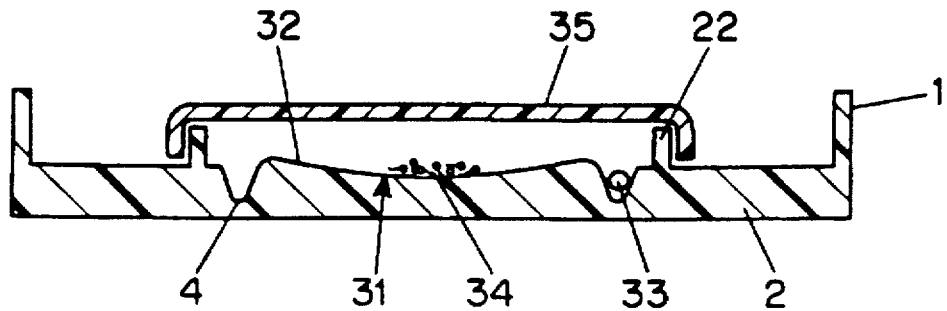
FIG. 3 shows a sectional side view of a culture dish in accordance with the invention.

The oocyte chambers of the invention can be simple depressions, as shown in FIG. 3, or they may have a vortex shape. In the latter case, the oocyte chambers have a top diameter of from 200 to 5,000, preferably 400 to 1,000 microns, a bottom diameter of from 200 to 2,000, preferably from 200 to 500 microns and a depth of from 150 to 1,000, preferably from 150 to 500 microns.

The microchamber configuration shown in FIG. 1 can also be established by forming a raised border on the surface of, e.g. a plastic dish about the periphery of the microdrop. Oocyte chambers can be annexes formed in this raised border or depressions as discussed above.

In addition to the elements discussed above which actively participate in the IVF process the chambers may also include a well around the chamber to provide a source of water vapor to reduce evaporation. The well is not contiguous with the microchamber but would be situated under the cover along with the microchamber.

The method of the present invention is useful for achieving in vitro fertilization of human oocytes as well as oocytes from animals. These oocytes have a variety of sizes, ranging from about 80 to about 150 microns in diameter. For example, human oocytes are generally about 120 microns in diameter, while oocytes from mice and rats are generally about 80 microns in diameter. As used herein, the term "oocyte" may also encompass oocytes together with the surrounding cumulus cells, or small clusters of oocytes which are retrieved together and cannot be separated.

The oocytes to be fertilized are manually placed into oocyte chambers, for example by micropipetting as is normally used to load eggs for standard insemination. The oocyte chambers are sized for the particular species of oocyte to be fertilized. In order to avoid damage to the oocyte and yet obtain efficient fertilization, the volume of the chamber is generally from 800 to 2,000% of the volume of the oocyte. A suitable chamber size for use with a number of species, including man, has dimensions of 200 µDiameter×400µ depth.

The particular medium employed within the culture dish is not critical, and any medium known to be appropriate for a particular species may be used. For example, successful results have been obtained using the human media shown in Table 2.

EXAMPLE 3

Frozen-thawed mouse sperm were used to study the utility of the prototype device as shown in FIG. 1, because most murine sperm fail to survive freezing. In the test, oocytes were zona drilled as described in Gordon et al., J. Exp. Zool. 239, 347 (1986) to assist the few motile sperm to penetrate the oocyte and then placed individually into oocyte chambers formed in a microdrop of the fertilization medium shown in Table 3. A 10 µl sample of frozen-thawed sperm was then deposited in the center of the microdrop. Over five experiments in which the percentage of motile sperm was less than 5%, an average of 65% fertilization (range 53–76%) was achieved.

TABLE 2

Fertilization Medium for In Vitro Fertilization of Human Oocytes

| COMPONEMT (mg/L) | F-10 (1x) | Eagle's Medium (1x) |
|---|---|---|
| INORGANIC SALTS: | | |
| CaCl₂ (anhyd.) | — | 200.00 |
| CaCl₂.2H₂O | 44.1 | — |
| CuSO₄.5H₂O* | 0.0025 | — |
| FeSO₄.7H₂O | 0.834 | — |
| KCl | 285.0 | 400.00 |
| KH₂PO₄ | 83.0 | — |
| MgSO₄.7H₂O | 152.8 | 200.00 |
| NaCl | 7400.0 | 6800.00 |
| NaHCO₃ | 1200.0 | 2200.00 |
| NaH₂PO₄.H₂O | — | 140.00 |
| Na₂HPO₄.7H₂O | 290.0 | |
| ZnSO₄.7H₂O | 0.0288 | |
| OTHER COMPONENTS: | | |
| D-Glucose | 1100.0 | 1000.00 |
| Hypoxanthine | 4.0 | — |
| Lipoic acid | 0.2 | — |
| Phenol red | 1.2 | 10.00 |
| Sodium pyruvate | 110.0 | |
| Thymidine | 0.7 | |
| AMINO ACIDS: | | |
| L-Alanine | 9.0 | — |
| L-Arginine | — | 17.40 |
| L-Arginine HCl | 211.0 | — |
| L-Asparagine.H₂O | 15.01 | |
| L-Aspartic acid | 13.0 | |

TABLE 2-continued

Fertilization Medium for In Vitro Fertilization of Human Oocytes

| COMPONEMT (mg/L) | F-10 (1x) | Eagle's Medium (1x) |
|---|---|---|
| L-Cysteine | 25.0 | |
| L-Cystine | — | 12.00 |
| L-Glutamic acid | 14.7 | |
| L-Glutamine | 146.00 | 292.00 |
| Glycine | 7.51 | |
| L-Histidine | — | 8.00 |
| L-Histidine HCl.H₂O | 23.0 | |
| L-Isoleucine | 2.6 | 26.00 |
| L-Leucine | 13.0 | 26.00 |
| L-Lysine | — | 29.20 |
| L-Lysine HCl | 29.0 | — |
| L-Methionine | | 7.50 |
| L-Phenylalanine | | 16.50 |
| L-Threonine | | 24.00 |
| L-Tryptophane | | 4.00 |
| L-Tyrosine | | 18.00 |
| L-Tyrosine (Disodium salt) | | — |
| L-Valine | | 23.50 |
| VITAMINS: | | |
| Biotin | 0.024 | 1.00 |
| Choline bitartrate | — | 1.00 |
| Choline chloride | 0.698 | 1.00 |
| Folic acid | 1.32 | 1.00 |
| i-Inositol | 0.541 | 2.00 |
| Nicotinamide | | 1.00 |
| Pyridoxal HCl | | 1.00 |
| Riboflavin | 0.376 | 0.10 |
| Thiamine HCl | 1.00 | 1.00 |
| D-Ca-pantothenate | 0.715 | |
| Niacinamide | 0.615 | |
| Pyridoxine HCl | 0.206 | |
| Vitamin B₁₂ | 1.36 | |

TABLE 3

| | |
|---|---|
| NaCl (Mallinckrodt #7851) | 5.14 grams |
| KCl (Baker #I-3040) | 0.36 grams |
| KH₂PO₄ (Mallinckrodt #7100) | 0.16 grams |
| MgSO₄-7H₂O (Mallinckrodt #6066) | 0.29 grams |
| NaHCO₃ (Fischer #S-233) | 2.11 grams |
| Na Pyruvate (Schwartz-Mann #904144) | 0.04 grams |
| Glucose (Fischer #D-16) | 1.00 grams |
| Penicillin G, K salt (Schwartz-Mann #4049) | 0.75 grams |
| Streptomycin sulfate (Schwartz-Mann #3242) | 0.05 grams |
| Weigh these ingredients into a flask, add 995 ml double distilled H₂O, and stir until dissolved. Then add | |
| Sodium lactate 60%, Pfanstiehl Labs | 3.68 ml |
| Phenol red, 1% solution (Difco #5358-59) | 1.00 ml |
| To this add 3 grams/liter crystalline bovine serum albumin (Pentex #81-001-3) and stir until dissolved. This medium is filtered through an 0.22 micron Millipore filter for sterilization and may be stored at 4° C. | |

For comparison zona drilled mouse oocytes were exposed to the same volume of frozen-thawed sperm in a 2 ml tissue dish. In this environment, a fertilization rate of only 3% was observed, probably because the many immotile sperm blocked access to the oocyte.

The improved efficiency of in vitro fertilization in the culture dish of the invention makes it feasible to preserve valuable mouse strains such as transgenic lines by sperm cryopreservation. Thus, the present invention may prove a valuable tool in the management of valuable animal strains.

EXAMPLE 4

Sperm from vasectomized male mice that had proven sterile for more than six months were tested in a shaped microdrop as shown in FIG. 1. A total of 30 oocytes were placed in the oocyte chambers and a 10 μl sample of unfractionated sperm was added. The fertilization medium was that shown in Table 3.

In two experiments, the fertilization efficiency was 100%, including one experiment in which very few free swimming sperm were present. In contrast, only 7% of oocytes were fertilized using the same sperm samples when $10^6$ motile sperm were added to a 2 ml dish of culture medium.

These results indicate that the present invention can improve fertilization efficiency in cases where the percentage of motile sperm is very low, i.e. <10%. The invention may prove especially useful in clinical situations such as a congenital absence of the vas deferens or failed vasectomy repair. Further, because fractionation is unnecessary, use of the present invention can be used to simplify "routine" in vitro fertilization.

EXAMPLE 5

The microchamber of FIG. 1 was used to inseminate oocytes with a sperm sample obtained from a human patient with congenital absence of the vas deferens. After recovery and washing, this sample had only $1 \times 10^6$ sperm with approximately 5% motility and was grossly contaminated with blood. The washed sample without fractionation was used to inseminate 2 oocytes in the microchamber and the remainder of the sample was fractionated using the percoll technique.

After percoll fractionation, no motile sperm were recovered for insemination of oocytes not placed in the microchamber. However, 1 of 2 eggs (50%) in the micro-chamber were fertilized with the unfractionated preparation and an embryo transfer was accomplished.

EXAMPLE 6

In other studies standard inseminations have been carried out by loading human eggs in the microchamber of FIG. 1. Sperm were either washed or diluted and added directly to the chambers, and the fertilization rates were compared to normal control inseminations in 2 ml dishes following the "swim-up" procedure. In one patient with $80 \times 10^6$ motile sperm in the ejaculate, the sperm were simply diluted and placed in the microchamber. In the control, 2 washes followed by swim up was performed, a process requiring nearly 2 hours and resulting in significant sperm loss. Results were better in the microchamber (¾ eggs fertilized) then in the control (⅙ fertilized) thus showing that the microchamber can eliminate the time, expense and sperm loss associated with washing and fractionation.

In several additional experiments, sperm were washed and used in the microchamber without fractionation. Fertilization rates have been the same in the microchamber (9/28, 32%) as in control dishes (15/56, 27%), again showing that the microchamber eliminates the need for fractionation.

EXAMPLE 7

Semen was collected from 19 male patients who provided sperm for other laboratory tests, for in vitro fertilization or intrauterine insemination. In three additional experiments, various concentrations of sperm which has been processed for the zona-free hamster penetration assay (SPA) were utilized and compared with standard SPA results.

For the sperm penetration assay, female hamsters aged 6–8 weeks were superovulated by intraperitoneal injection of 15 international units (IU) of pregnant mares' serum (Sigma No. G-4877, St. Louis, Mo.), followed 52 hrs. later by intraperitoneal injection of 30 IU human chorionic gonadotrophin (Sigma, St. Louis, Mo., No. CG-5). Sixteen hours after HCG females were sacrificed by $CO_2$ inhalation, and oviducts and ovaries were removed to normal saline. Cumulus cells were removed by treatment for 5 min. at 37° C. with 0.1% hyaluronidase (Sigma, St. Louis, Mo., No. H-3757) dissolved in phosphate buffered saline. Subsequently, oocytes with identifiable first polar bodies were collected and the zonae pellucidac were removed by exposure to 0.1% pronase (Sigma, St. Louis, Mo., No. P-6911), dissolved in PBS, for 3–5 minutes at room temperature. Eggs were washed 3 times in BWW medium (Irvine Scientific, Santa Ana, Calif., No. 9087), and 5–15 oocytes were loaded into each side well of the in vitro fertilization microchamber.

Figure 5:
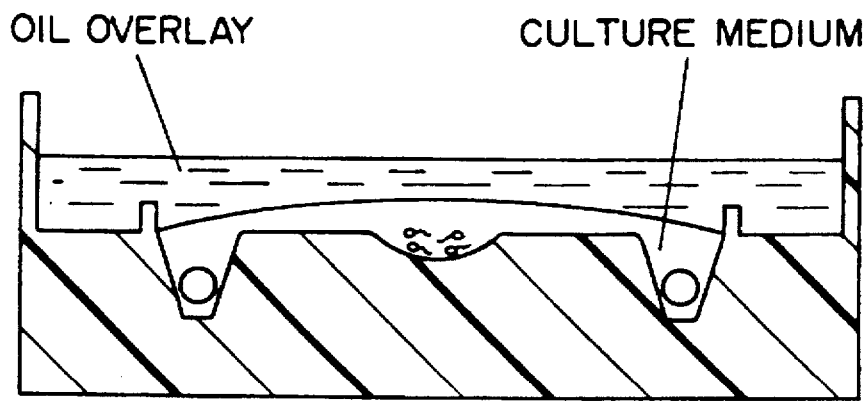
FIG. 5 shows a sectional side view of a culture dish in accordance with the invention.

The microchamber was fashioned from clear Lucite. In the center of the chamber, which is similar to a petri dish (FIG. 5), a circular area about 16 mm in diameter was delimited by a ridge with a thickness and height of about 0.9 mm. Around the central point of the dish surface a shallow depression, 0.925 mm deep and 7 mm in diameter was made. This area was utilized for sperm loading. At the periphery of the circle defined by the ridge, side wells for oocyte loaded were placed. These side chambers had a diameter at the dish surface of 3.95 mm, a diameter at the base of 1 mm, a depth of about 3 mm, and a wall slope of 53°. These side wells thus were shaped like inverted cones. The outer edges of the side chambers made direct contact with the plastic ridge, such that sperm could not swim between the ridge, which defined the limits of the culture drop, and the side chamber. Microchambers containing 2,4, and 8 side wells were constructed. FIG. 5 shows a cross section of the chamber, illustrating 2 side wells.

After filling the microchamber to capacity with 200 μl of medium and covering the medium with mineral oil (Sigma, St. Louis, Mo., No. M-3516) side wells were loaded with zona-free hamster oocytes (5–10 eggs per side well), and 6–10 μL. of unprocessed semen was added to the central depression. Microchambers were then incubated for 3–4 hrs. at 37° C in 5% $CO_2$ in air and 95% humidity. Eggs were then harvested and washed with BWW medium. A cover slip was placed over the slide and pressed gently to flatten the eggs. Eggs were then fixed in 3% glutaraldehyde (Sigma, St. Louis, Mo., No. G-6257), and stained with 0.5% acetocarmine dissolved in 45% glacial acetic acid. The cover slips were then sealed and the eggs examined at 400× magnification under phase contrast optics. A positive penetration was recorded with either a swollen sperm head or pronucleus, associated with a sperm tail, was observed (2).

In three additional cases sperm were processed as is routinely done with the enhanced SPA (2). Briefly, sperm were mixed with an equal volume of test yolk buffer (Irvine Scientific, Santa Ana, Calif., No. 9972) and incubated for 48 hrs. at 4° C. Sperm were then washed twice in BWW medium with centrifugation for 10 min. at 250×g. For the standard SPA these sperm were then added to zona-free oocytes at a concentration of $5 \times 10^6$ sperm/ml. The sample was also diluted to varying degrees for insemination in the microchamber.

Because capacitation is considered an absolute requirement for hamster egg penetration by human sperm (1–5) a single penetration event was considered as positive evidence of capacitation. Table 4 presents results of insemination in the microchamber in 19 cases. Where possible, results of concomitant tests of sperm quality, carried out with the remainder of the even distribution of sperm throughout the 200 μl microdrop, is also shown. Remarkably, penetration was observed in 12/19 (64%) of tests, even though the sperm were not washed or incubated for any period of time prior to insemination.

Penetration was unequivocal. The histological evidence of penetration fit all established criteria for a positive SPA. Not only were penetrations clearly documented in the 12 cases, but they occurred after insemination by fewer sperm than are customarily employed for the enhanced SPA (i.e., $5 \times 10^6$/ml). Penetration did not occur when the final sperm concentration in the microchamber was less than $1 \times 10^6$/ml (Cases 3, 13 and 17, Table 1). In some cases failed hamster penetration could be attributed to poor sperm quality. For example, in case 5 penetration did not occur in the microchamber, but the enhanced SPA performed with the same sample also gave suboptimal penetration. In cases 8 and 13, IVP results were poor, with 2/12 (17%) of eggs fertilized in case 8, and 2/8 (25%) in case 13. Although the enhanced SPA was not performed on these patients, the poor fertilization of human eggs suggests sperm dysfunction that could compromise the ability of the sperm to penetrate the hamster oocyte. Only in case 11 was there failed penetration in the chamber with all other findings indicating that the sperm were normal.

Because hamster penetration was seen with lower sperm counts than are normally employed for the SPA, it is hypothesized that the chamber might concentrate fertilizable sperm in the side wells in addition to selecting these sperm from other components of semen. As a preliminary test of this possibility, three additional experiments were performed wherein sperm were processed for the enhanced SPA, but added to the microchamber at lower concentrations than are normally employed for the SPA. In all three cases penetration was observed, and in one instance hamster oocyte penetration was documented after insemination with a final concentration of 125,000 sperm/ml. This is 40-fold fewer sperm than are normally used for the SPA.

chamber can also be used to harvest sperm for micromanipulation. When sperm counts are extremely low, the current favored procedure for assisting fertilization by micromanipulation in intracytoplasmic sperm injection (ICSI). With this procedure, motile sperm are purified by Percoll gradient centrifugation, and then picked up individually for insertion into oocytes. However, when sperm counts are low (e.g. $20 \times 10^6$/ml or substantially less) the fractionation procedure can result in failure to obtain even one motile sperm for ICSI. This is due in part to the fact that sperm are lost during fractionation, but also, that sperm from such abnormal samples are more sensitive to damage by centrifuging.

To address these problems the ability of the microchamber to sort motile sperm from oligospermic samples for subsequent use in ICSI was studied. In one case a sample containing only 30,000 motile sperm per milliliter of ejaculate was used. When 10 µl of this sample was loaded into the microchamber (i.e., containing only 300 motile sperm), more than 50 motile sperm were harvested from the sidewells after a four hour incubation period. Similar results have been obtained with samples ranging in count from 60,000 to 200,000 motile sperm.

These results indicate that when ICSI is to be performed, it is necessary only to load a sample of ejaculate into the microchamber on the morning of the case, and then to harvest sperm several hours later, when ICSI is normally performed. This capability could substantially improve the ICSI procedure.

The foregoing discussion and examples set forth basic parameters for the method and apparatus of the invention. It will be apparent, however, that other configurations could also be employed. For example, as compared to FIG. 5, a culture dish having one or more oocyte chambers 4 disposed on a central plateau region 51 surrounded by an annular well 52 into which sperm are loaded could also be used in the

TABLE 4

Results of hamster penetration test performed with unprocessed semen in the in vitro fertilization microchamber

| Case Number | Total Count ($\times 10^6$/ml) | Motility (%) | Volume added (uL) | Mot. Sperm Conc. ($\times 10^6$/ml) | Chamber SPA | Standard SPA | IVF Fert. | IUI Results (HCG) |
|---|---|---|---|---|---|---|---|---|
| 1 | 99 | 66 | 6 | 1.9 | + | N/A | 19/22 | N/A |
| 2 | 74 | 46 | 10 | 1.7 | + | N/A | N/A | N/A |
| 3 | 43 | 24 | 10 | 0.5 | − | N/A | N/A | N/A |
| 4 | 160 | 67 | 8 | 4.2 | + | N/A | N/A | N/A |
| 5 | 57 | 47 | 10 | 1.3 | − | Weak + | N/A | N/A |
| 6 | 101 | 79 | 10 | 4.0 | + | N/A | 9/9 | N/A |
| 7 | 97 | 57 | 10 | 2.7 | + | N/A | N/A | N/A |
| 8 | 97 | 88 | 10 | 4.2 | − | N/A | 2/12 | N/A |
| 9 | 48 | 75 | 10 | 1.8 | + | N/A | 20/21 | N/A |
| 10 | 86 | 76 | 10 | 3.2 | + | N/A | N/A | — |
| 11 | 110 | 51 | 10 | 2.8 | − | + | N/A | N/A |
| 12 | 67 | 49 | 10 | 1.6 | + | N/A | N/A | — |
| 13 | 24 | 49 | 10 | 0.9 | − | N/A | 2/8 | N/A |
| 14 | 91 | 32 | 10 | 1.4 | − | N/A | N/A | N/A |
| 15 | 36 | 55 | 10 | 1.0 | + | N/A | N/A | — |
| 16 | 84 | 58 | 10 | 2.4 | + | N/A | N/A | N/A |
| 17 | 39 | 46 | 10 | 0.9 | − | N/A | N/A | N/A |
| 18 | 60 | 67 | 10 | 2.0 | + | N/A | N/A | + |
| 19 | 73 | 42 | 10 | 1.5 | + | N/A | N/A | N/A |

EXAMPLE 8

Because the sidewells of the microchamber concentrate motile sperm directly from unprocessed samples, the microchamber method of the invention. The central plateau 51 advantageously may have a surface level which is below the interior surface of the base portion.

What is claimed is:

1. A container for concentrating motile sperm in a microchamber, said container comprising a base, said base comprising at least one microchamber and shaped such that fertilization medium, when placed in the container, fills said at least one microchamber and a portion of the container outside of said at least one microchamber, and further such that the medium extends from said portion to said at least one microchamber said at least one microchamber being formed and positioned in relation to the remainder of said container such that sperm of normal motility, when placed in said portion outside and remote from the microchamber, will tend to swim into the microchamber, said microchamber being shaped such that motile sperm which swim from said portion into said microchamber tend to be retained in said microchamber.

2. A container according to claim 1 for achieving in vitro fertilization of an oocyte, wherein said microchamber is formed and positioned in relation to the remainder of the container such that sperm of normal motility, when placed in said container remote from said microchamber, will tend to congregate in the vicinity of the microchamber and permit contact between an oocyte contained in said microchamber and said sperm.

3. A container according to claim 2, wherein said container comprises a culture dish having a base portion and a side portion, wherein the base portion of the dish has disposed on the interior surface thereof a plurality of microchambers, and wherein said microchambers are disposed about the periphery of a central region having a diameter of from 0.5 to 3.0 cm.

4. A container according to claim 3, wherein the microchambers have a diameter of about 200 µm and a depth of about 400 µm.

5. A container according to claim 3, wherein the microchambers are depressions formed in the upper surface of the base portion of the dish.

6. A container according to claim 5, wherein the central region has a depression at its center such that the depth of a liquid placed in the center is greater at the center than at the periphery of the central region.

7. A container according to claim 5, wherein guide members are formed on the interior surface of the base portion of the dish, said guide members being positioned so that they tend to direct motile sperm placed in the central circular region to swim toward the microchambers.

8. A container according to claim 7, wherein the central circular region has a depression at its center such that the depth of a liquid placed in the center is greater at the center than at the periphery of the central circular region.

9. A container according to claim 7, wherein the microchambers are vortex-shaped.

10. A container according to claim 9, wherein the microchambers have a top diameter of from 200 to 5000 microns, a bottom diameter of from 200 to 2000 microns and a depth of from 150 to 1000 microns.

11. A container according to claim 10, wherein the central circular region has a depression at its center such that the depth of a liquid placed in the center is greater at the center than at the periphery of the central circular region.

12. A container according to claim 1, for in vitro fertilization, said container comprising a base portion and a side portion wherein the base portion has disposed on the interior surface thereof an annular well region defining a central plateau, said plateau having a surface level below the interior surface of the base portion and wherein one or more oocyte chambers are formed on the central plateau.

13. A container according to claim 12, wherein the oocyte chambers have a diameter of about 200 µm and a depth of about 400 µm.

14. A container according to claim 1 comprising a base having an upper surface, said upper surface having a central area defined by a ridge, said area having a central portion comprised of a shallow depression for loading of a sperm sample, and at least one microchamber located at the periphery of the area.

15. A container according to claim 14, wherein said at least one microchamber is adjacent said ridge such that sperm cannot swim between the ridge, which defines the limits of the area, and the microchamber.

16. A container according to claim 15, wherein the said at least one microchamber is shaped like an inverted cone.

17. A container according to claim 15, wherein there are a plurality of said microchambers.

18. A container according to claim 15, wherein the area is shaped and depressed below the upper edge of the ridge such that the fertilization medium can cover substantially the entire area defined by the ridge.

19. A container according to claim 15, wherein said base is comprised of plastic.

20. A container according to claim 19, wherein said base is comprised of lucite.

21. A container according to claim 14, wherein the said at least one microchamber is shaped like an inverted cone.

22. A container according to claim 14, wherein there are a plurality of said microchambers.

23. A container according to claim 14, wherein the area is shaped and depressed below the upper edge of the ridge such that the fertilization medium can cover substantially the entire area defined by the ridge.

24. A container according to claim 14, wherein said base is comprised of plastic.

25. A container according to claim 24, wherein said base is comprised of lucite.

* * * * *